US00PP10964P

United States Patent [19]

Danziger

[11] Patent Number: Plant 10,964

[45] Date of Patent: Jun. 22, 1999

[54] GYPSOPHILA PLANT NAMED 'DANGYPMINI'

[75] Inventor: Gabriel Danziger, Nir Zvi, Israel

[73] Assignee: Danziger—"Dan" Flower Farm, Post Beit Dagan, Israel

[21] Appl. No.: 08/966,017

[22] Filed: Nov. 7, 1997

[51] Int. Cl.[6] ..... A01H 5/00

[52] U.S. Cl. ..... Plt./354

[58] Field of Search ..... Plt./68.1

*Primary Examiner*—Elizabeth Kemmerer

*Attorney, Agent, or Firm*—Foley & Lardner

[57] ABSTRACT

A new and distinct cultivar of gypsophila plant named 'Dangypmini', characterized by the combined features of miniature, luminous white, fully double flowers, fully branched flowering stem, head spray type, secondary cluster arrangement, fast growing habit, and its suitability for both indoor and outdoor cultivation.

2 Drawing Sheets

The present invention comprises a new and distinct cultivar of gypsophila, botanically a *Gypsophila paniculata* hybrid, referred to by the cultivar name 'Dangypmini'.

The new cultivar 'Dangypmini' was developed by the inventor in a controlled breeding program carried out in Mishmar Hashiva, Israel in 1995. Both the male and female parents of 'Dangypmini' were *Gypsophila paniculata* cultivars unknown at this time. Both parents are proprietary cultivars used in the breeding program.

'Dangypmini' was discovered and selected as a flowering plant within the progeny of the stated cross by the inventor in Mishmar Hashiva, Israel. The first act of asexual reproduction was by terminal or stem cuttings taken at Mishmar Hashiva, Israel in May 1995 by a technician working under the supervision of the inventor. That and subsequent asexual reproduction have clearly demonstrated that the unique features of this new gypsophila cultivar are firmly fixed and are retained through successive propagation. The phenotype may vary somewhat with variations in environment such as temperature, light intensity, and day length, however, without any variations in genotype.

The following observations, measurements and comparisons describe plants grown in Mishmar Hashiva, Israel under conditions which approximate those generally used in commercial practice. The following traits have been repeatedly observed and are determined to be basic characteristics of 'Dangypmini' which in combination distinguish this gypsophila as a new and distinct cultivar.

1. Fully branched flowering stem.
2. Head spray type, secondary cluster arrangement.
3. Miniature (4–5 mm), luminous white, fully double flowers.
4. Delicate, stable stems.
5. Fast growing.
6. Long vase life.
7. Suitable for both indoor and outdoor cultivation.
8. Can be grown all year round if proper cultivation practices are provided.

Of the commercial cultivars known to the inventor, there is no cultivar with which 'Dangypmini' can be meaningfully compared. The combined features of 'Dangypmini' make it a unique new cultivar.

Figure 1:
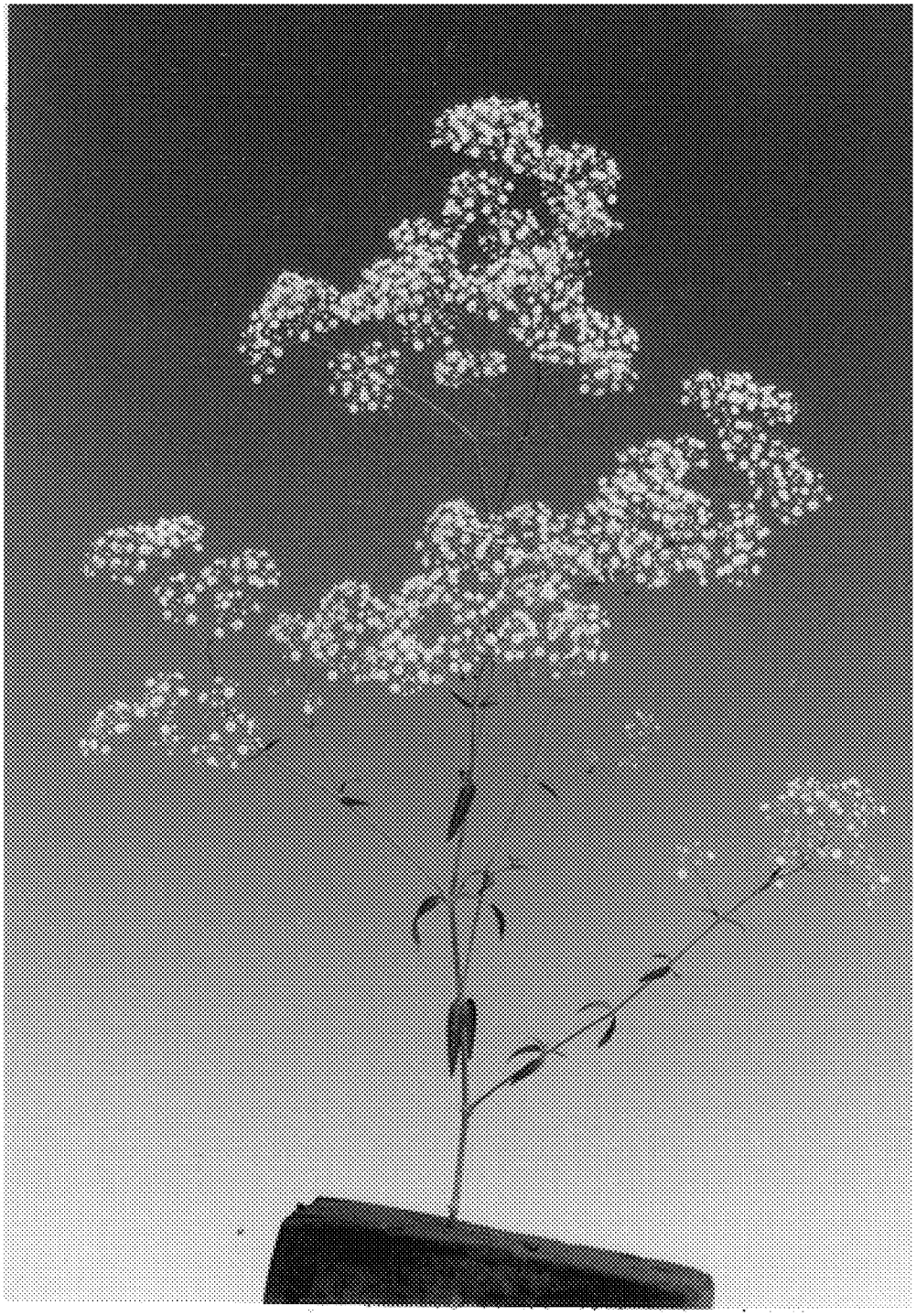
Figure 2:
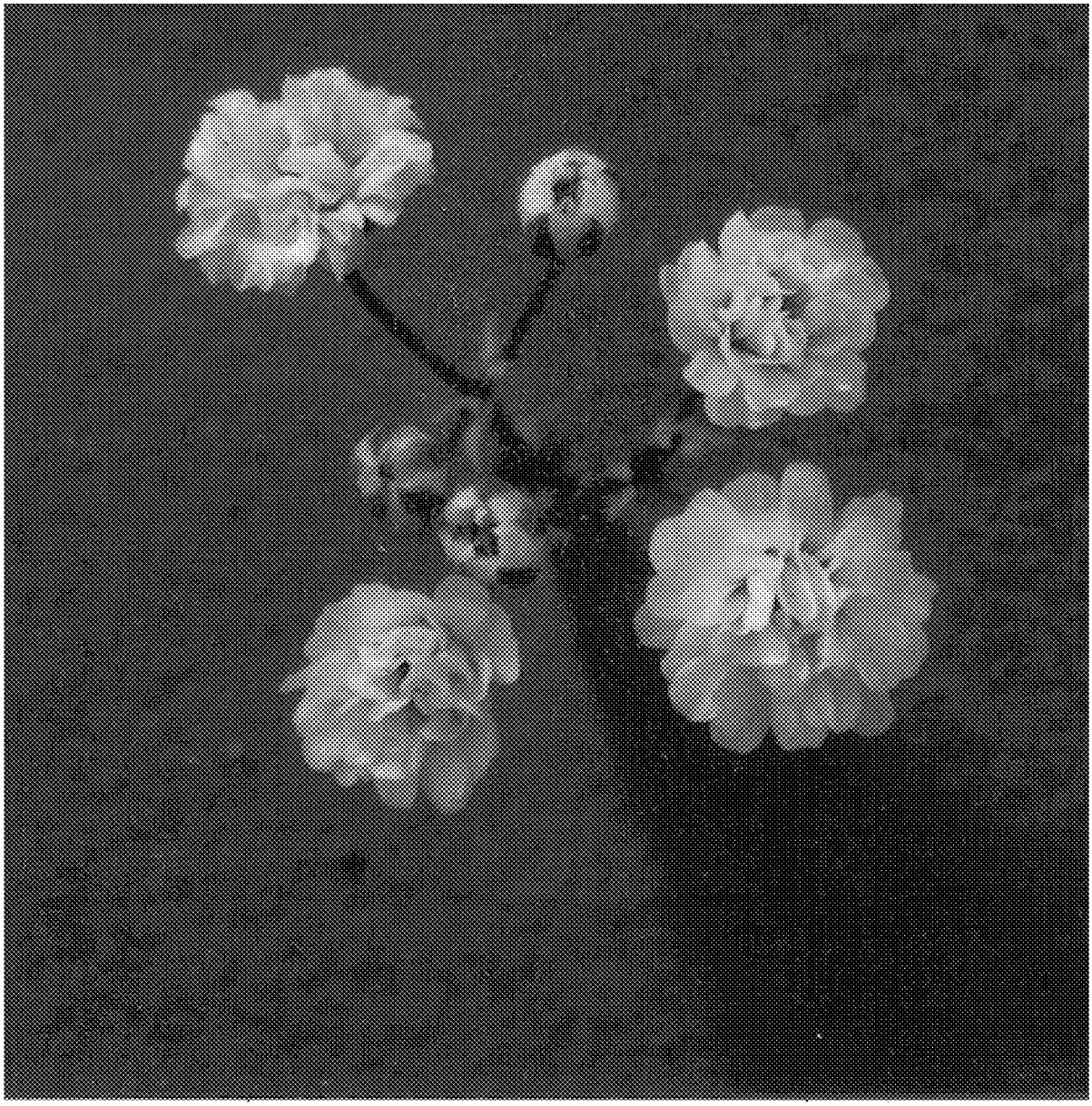

In the accompanying color photographs, FIG. 1 comprises a side elevation of a typical flowering stem of the new cultivar. FIG. 2 comprises a greatly enlarged top view showing clusters of the small fully double flowers. The colors in the photographs are as true as is reasonably possible to obtain in colored reproductions of this type.

The following is a detailed description of the new cultivar based on plants produced under commercial practice in Mishmar Hashiva, Israel.

Color references are made to The Royal Horticultural Society Colour Chart (R.H.S.) except where general terms of ordinary dictionary significance are used.

Classification:

*Botanical*.—A hybrid of *Gypsophila paniculata*.

*Commercial*.—Gypsophila cultivar 'Dangypmini'.

Plant:

*General appearance*.—Form: Upright and spreading. Habit of growth: Vigorous growth habit with fully branded flowering stem.

*Foliage*.—Leaves: Size: 5–6 cm. Shape: Lanceolate. Margin: Entire Color (top): 139 A. Color (bottom): 137 A. Stipules: None.

Flowering description:

*Natural flowering season*.—All year round under proper cultivation practices.

*Flower buds*.—Small and round turning white after opening.

*Flowers Borne*.—Panicled.

*Quantity of flowers*.—Very floriferous; hundreds per stem.

*Petals*.—Shape: Spatulate. Color: White, 155 D Petal markings: None. Number of petals: About 50 per flower. Size of flowers: Very small, 4–5 mm in total diameter.

*Reproductive organs*.—The new cultivar is sterile so that no reproductive organs can be observed.

Disease resistance: To date, the new cultivar has not shown any abnormal susceptibility to disease.

I claim:

1. A new distinct cultivar of gypsophila plant named 'Dangypmini', as illustrated and described.

* * * * *